US010195447B2

(12) United States Patent
Sumners et al.

(10) Patent No.: US 10,195,447 B2
(45) Date of Patent: Feb. 5, 2019

(54) METHOD FOR STIMULATING MUSCLES OF A SUBJECT AND APPARATUS FOR PERFORMING THE SAME

(71) Applicant: Actegy Limited, Ascot, Berkshire (GB)

(72) Inventors: David Paul Sumners, Walton on Thames (GB); Katya Nikolova Mileva, London (GB)

(73) Assignee: Actegy Limited (GB)

(*) Notice: Subject to any disclaimer, the term of this patent is extended or adjusted under 35 U.S.C. 154(b) by 17 days.

(21) Appl. No.: 14/111,912

(22) PCT Filed: Mar. 27, 2013

(86) PCT No.: PCT/GB2013/000134
§ 371 (c)(1),
(2) Date: Oct. 15, 2013

(87) PCT Pub. No.: WO2013/144544
PCT Pub. Date: Oct. 3, 2013

(65) Prior Publication Data
US 2014/0107729 A1    Apr. 17, 2014

(30) Foreign Application Priority Data
Mar. 28, 2012 (GB) .................................. 1205451.6

(51) Int. Cl.
*A61N 1/00* (2006.01)
*A61N 1/372* (2006.01)
*A61N 1/36* (2006.01)

(52) U.S. Cl.
CPC ....... *A61N 1/3727* (2013.01); *A61N 1/36003* (2013.01); *A61N 1/36021* (2013.01)

(58) Field of Classification Search
CPC .............. A61N 1/36003; A61N 1/3727; A61N 1/36021; A61N 1/36146; A61N 1/3615;
(Continued)

(56) References Cited

U.S. PATENT DOCUMENTS 2,532,788 A   12/1950  Sarnoff
4,492,233 A *  1/1985  Petrofsky et al. .............. 607/48
(Continued)

FOREIGN PATENT DOCUMENTS

GB    2136297 A      9/1984
WO    20070113775 A2   10/2007
WO    2008086411 A2    7/2008

OTHER PUBLICATIONS

International Search Report, PCT App. No. PCT/GB2013/000134, dated Jul. 16, 2013, 5 pages.
(Continued)

*Primary Examiner* — Mallika D Fairchild
(74) *Attorney, Agent, or Firm* — Arnold & Saunders, LLP; Jason Saunders; Christopher McKeon

(57) ABSTRACT

A method of electrostimulation of a group of one or more target muscles of a subject is provided, the method comprising in a first step applying to the subject an electrical pulse having a duration of at least 0.5 milliseconds and an intensity below that effective in stimulating contraction of the target muscles of the subject; and in a second step applying one or more electrical pulses at an intensity sufficient to stimulate contraction of the target muscles of the subject. An apparatus for the electrostimulation of the muscles of a subject employing the aforementioned method is also provided.

17 Claims, 3 Drawing Sheets

(58) Field of Classification Search
CPC ............ A61N 1/36153; A61N 1/36157; A61N 1/36164; A61N 1/36175; A61N 1/36178; A61N 1/36189; A61N 1/36192; A61N 1/36196
See application file for complete search history.

(56) References Cited

U.S. PATENT DOCUMENTS

| | | |
|---|---|---|
| 6,343,232 B1 | 1/2002 | Mower |
| 6,393,328 B1 | 5/2002 | McGraw et al. |
| 2005/0283204 A1 | 12/2005 | Buhlmann et al. |
| 2006/0174522 A1* | 8/2006 | Yu ............................ A43B 3/00 36/141 |
| 2011/0288602 A1 | 11/2011 | Nachum et al. |

OTHER PUBLICATIONS

Search Report, GB App. No. 1205451.6, dated Jul. 16, 2012, 2 pages.

* cited by examiner

METHOD FOR STIMULATING MUSCLES OF A SUBJECT AND APPARATUS FOR PERFORMING THE SAME

The present invention relates to a method of stimulating the muscles of a subject and to an apparatus for performing the same.

The electrical stimulation of the muscles of a subject is known in the art. Electrical stimulation of the muscles is achieved by applying one or more electrodes to the subject, typically to the skin in the region of the muscles to be stimulated. Electrical pulses are applied to the subject through the electrodes, which in turn stimulate the muscles to contract. It is known to apply electrical stimulation by means of a train of pulses having a range of different patterns, including a uniform pulse length and pulse separation.

Apparatus and devices for such electrical stimulation are known and commercially available. One such apparatus is the Circulation Booster™ available from High Tech Health Limited, UK (now Actegy Limited). The apparatus comprises an electrically conductive pad, onto which the user places a foot. Pulses of electrical current are applied to the soles of the feet through the pad, which induce the muscles in the foot and leg of the subject to contract. The pulses of electrical current may be applied in a number of different patterns and at different current levels, according to the treatment required and the condition of the subject.

Methods and apparatus for the electrical stimulation of the muscles of a subject are also known in the literature.

U.S. Pat. No. 4,528,984 discloses an autoprogrammable functional electrical stimulation apparatus and a method of operating the same. The apparatus provides the functional electrical stimulation (FES) of muscles or muscle groups of a subject by applying electrical pulses. The apparatus is manually operable to control the amplitude of the electrical pulses to provide a desired FES regime. This regime is stored in the apparatus and is reproduced by a processor, to apply the desired pulse regime to the subject.

U.S. Pat. No. 4,712,558 concerns an investigative method and apparatus for the electrical stimulation of the muscles of a subject. U.S. Pat. No. 4,712,558 discusses recording the electromyographic responses of a muscle when stimulated, for example by neural or electrical stimulation. The electromyographic responses typically include so-called motor unit action potentials or MUAPs. U.S. Pat. No. 4,712,558 reports on the investigation of MUAP discharge sequences and their analysis, in particular that the MUAP responses comprise two elements of information: first the information necessary to generate the stimulus needed for contraction of the muscle and resulting movement of joints to which the muscle is attached; and second the information for generating an intracellular environment within the muscle tissue for biosynthesis. This information is employed in U.S. Pat. No. 4,712,558 to generate an electrical signal for the artificial stimulation of the muscles of a subject. In the method of U.S. Pat. No. 4,712,558, electrical pulses are generated and applied to the subject, in particular by means of electrodes overlying the skin of the subject, the intervals between respective stimulating pulses being capable of being individually defined or varied.

In a further development of U.S. Pat. No. 4,712,558, U.S. Pat. No. 5,350,415 describes a method and apparatus for the trophic stimulation of muscles. The stimulation is achieved by applying a pattern of electrical pulses to the muscles of the subject, as in U.S. Pat. No. 4,712,558. U.S. Pat. No. 5,350,415 describes the application of sampled predictive running average analysis of the MUAP signals to generate a pulse sequence for electrical stimulation of muscle tissue. In particular, U.S. Pat. No. 5,350,415 discloses the generation of a pulse sequence having a continuous low-rate firing activity, described mathematically as a delta function continuously pulsing at a slow base rate with interpulse intervals in the range of from 120 to 200 milliseconds. This pattern has superimposed thereon a rectangular-like modulation with an exponential rise and fall, which quickly (that is within 20 to 40 milliseconds) changes the low base rate into a burst of high rate short pulses having a short interpulse interval (IPI) of from 20 to 40 milliseconds. The decrease in the IPI is maintained for about 40 milliseconds, that is for about three to four pulses, after which it is reduced exponentially to an IPI of from 60 to 80 milliseconds. Finally, after about 500 milliseconds, the IPI is further decreased to a base slow rate of 120 to 200 milliseconds. The entire cycle has a recurrence period of about 1 second. The train of electrical pulses having the aforementioned pattern is applied to the subject to stimulate the muscle activity.

More recently, WO 2008/086411 discloses an electrostimulation device to provoke the venous pumping of blood from the legs of a subject. The venous blood pumping is induced by applying to the subject short bursts of electrical impulses of high energy at a predetermined durational range, in which each burst has an associated modulated intensity and/or time duration. Particular pulse regimes disclosed in which pulses are spaced by intervals of 4 milliseconds. Superimposed on these pulses is a modulation pattern, in which the width of the pulses is first increased, to provide increasing energy applied to the subject, and thereafter decreased to reduce the energy being applied in each pulse. The impulse width of the high energy pulses is indicated to range from 26 to 240 microseconds. A so-called 'minimal energy' phase then follows, during which low energy pulses are applied, the low energy pulses having insufficient energy to stimulate contractions of the muscles. The pulse width of the low energy pulses is indicated in WO 2008/086411 to be from 5 to 40 microseconds. The low energy pulses are applied for a period of from 400 to 900 milliseconds. The low energy pulses are indicated to provide an electroanesthetization of the subject. It appears that the anesthetizing effect of these low energy pulses lasts only for the duration of the pulses.

US 2011/0288602 discloses a non-invasive method and device form promoting localised changes in blood flow through the blood vessels of a limb. The device applies electrical stimulation to the tissue by way of three separate electrodes, so as to induce muscle contraction. A similar method and device are disclosed in US 2007/0270917.

GB 2 136 297 concerns the electronic stimulation of muscles and employs an electrode harness for stimulating bodily movements in a human patient. A train of electrical pulses is applied to the patient through the harness. The voltage and spacing of the pulses in the pulse may be varied.

An automated adaptive muscle stimulation method and an apparatus for its implementation are disclosed in US 2005/0283204. The apparatus comprises at least one electrode assembly for delivering electrical signals to the subject to stimulate muscle action.

Finally, WO 2007/113775 discloses an apparatus for applying electrotherapy to a subject, in particular for providing transcutaneous nerve and/or muscle stimulation. The stimulation comprises a plurality of electrical pulses applied to the skin of the subject.

While much work has been devoted to developing systems and methods for the electrostimulation of a subject's muscles, there is still a need for an improved system and method.

As described above, electrostimulation is known to be applied to subjects to induce muscle contractions, in particular to promote the flow of blood through the vascular system of the subject. It has been found that a number of subjects find the intensity of the electrical pulses applied in the course of electrical stimulation in such techniques may be uncomfortable. It would therefore be advantageous if a method could be found to relieve the discomfort of such subjects arising from the electrostimulation treatment.

In addition, many subjects suffer from conditions giving rise to discomfort and pain, in particular in their limbs, such as their legs. It would be advantageous if a method could be found to reduce or alleviate such discomfort and pain and, in particular, if such a method could be combined with the electrostimulation of the muscles of the subject.

It has now been found that applying electrical pulses to the subject according to particular patterns or trains and at an intensity below that necessary to stimulate muscle contraction can reduce or eliminate the discomfort of a subsequent electrostimulation at higher intensities to promote muscle contraction. In addition, it has been found that the application of such low intensity electrical pulses can reduce or alleviate discomfort and pain arising from underlying conditions, at least for the duration of the electrostimulation treatment and more preferably for a longer period of time.

Accordingly, in a first aspect, the present invention provides a method of electrostimulation of a group of one or more target muscles of a subject, the method comprising:

in a first step applying to the subject an electrical pulse having a duration of at least 0.5 milliseconds and an intensity below that effective in stimulating contraction of the target muscles of the subject; and in a second step applying one or more electrical pulses at an intensity sufficient to stimulate contraction of the target muscles of the subject.

In a further aspect, the present invention provides an apparatus for the electrostimulation of the muscles of a subject, the apparatus comprising:

a generator for generating a plurality of electrical pulses;

means for applying the electrical pulses to the subject to induce contraction of at least one muscle of the subject;

wherein the generator is operable in a first step to apply to the subject a conditioning electrical pulse having a duration of at least 0.5 milliseconds and an intensity below that effective in stimulating contraction of the target muscles of the subject; and in a second step to apply to the subject one or more stimulating electrical pulses at an intensity sufficient to stimulate contraction of the target muscles of the subject.

The present invention provides an electrostimulation to the subject, by way of applying to the subject one or a series of electrical pulses to induce contraction in one or more muscles of the subject. The method of the present invention finds particular use in increasing blood flow in a range of vascular vessels, including the large blood vessels (arteries and veins) and the small blood vessels (tissue capillaries) of the subject. The method finds particular use in increasing the flow of blood in the feet and legs of the subject.

The method comprises a first step and a second step. In the first step, a conditioning pulse is applied to the subject. The pulse is applied at an intensity that is below the electrical intensity required for the muscle to be activated and begin to contract, that is below the motor threshold for the target muscles. The intensity of the pulse is determined by the electrical current applied and the applicable current may vary from subject to subject and from session to session for the same subject.

The intensity of the conditioning pulse is such as to provide an analgesic effect. To achieve this, as noted, the intensity of the pulses is required to be below the motor threshold intensity for the muscles of the subject undergoing treatment. The motor threshold intensity is the minimum pulse intensity required to produce excitation of the muscles of the subject. The motor threshold intensity will vary from subject to subject. For a given subject, the motor threshold intensity will vary for different muscles and for different muscle fibre types. In addition, the motor threshold intensity may vary according to the manner in which the pulses are being applied to the subject. For example, when applying electrical pulses transcutaneously, the motor threshold intensity will further depend upon such factors as the amount and nature of tissue between the surface of the skin and the underlying muscles, the condition of the skin layer, and the level of hydration of the subject, both locally at the site of electrical stimulation and systemically.

The motor threshold intensity may be considered to be that intensity of electrical pulse at which muscle contraction is caused to occur and the muscle induced to generate a force. This may be measured, for example using a force transducer. More preferably, the motor threshold intensity for a given site on a given subject may be determined in a simple manner. For example, the intensity of the electrical pulses being applied may be gradually increased from zero. The value of the intensity at which a visible muscle contraction is first observed may be taken to be the motor threshold intensity. As the intensity is increased above this value, muscle contraction will occur. Alternatively, the intensity of the electrical pulses may be increased until muscle action causes a visible movement in a joint to which the muscle is attached, for example in the case of electrical stimulation being applied to the feet and/or legs of a subject a visible raising of the heel or movement of a toe. In one regime, the intensity of the electrical pulses is increased from zero in increments, for example increments of 1% of the estimated motor threshold intensity, with each increment being held for a sufficient period of time to allow movement of the muscles and/or joints to become visible, for example at least 5 seconds, and the relevant muscles and/or joints observed for movement.

Accordingly, in a further aspect, the present invention provides a method of electrostimulation of a group of one or more target muscles of a subject, the method comprising:

in a preliminary step determining the motor threshold intensity of the target muscles of the subject by increasing the intensity of the pulse while monitoring one or more muscles for movement;

in a first step applying to the subject an electrical pulse having an intensity below that effective in stimulating contraction of the target muscles of the subject to provide an analgesic effect; and in a second step applying one or more electrical pulses at an intensity sufficient to stimulate contraction of the target muscles of the subject.

In a further aspect, the present invention provides an apparatus for the electrostimulation of the muscles of a subject, the apparatus comprising:

a generator for generating a plurality of electrical pulses;

means for applying the electrical pulses to the subject to induce contraction of at least one muscle of the subject;

wherein the generator is operable in a preliminary step to increase the intensity of the electrical pulse to allow a determination of the motor threshold intensity of the target area of the subject;

in a first step to apply to the subject a conditioning electrical pulse having an intensity below that effective in stimulating contraction of the target muscles of the subject but sufficient to induce an analgesic effect in the subject; and in a second step to apply to the subject one or more stimulating electrical pulses at an intensity sufficient to stimulate contraction of the target muscles of the subject.

The conditioning pulse is applied at an intensity below the motor threshold intensity and sufficient to induce an analgesic effect in the subject. In this respect, the intensity of the pulse may be considered to be the energy provided to the subject during the period of the electrical pulse. In the case of an electrical pulse applied at a fixed voltage, the intensity will vary according to the current applied during the period of the pulse and the duration of the pulse.

The conditioning pulse is preferably applied at an intensity up to 90% of the motor threshold intensity, more preferably up to 85% of the motor threshold intensity, still more preferably up to 80%. The conditioning pulse is preferably applied at an intensity of at least 10% of the motor threshold intensity, more preferably at least 20%, still more preferably at least 30%, for example at least 40%, preferably at least 50%. An intensity for the conditioning pulse of from 30 to 90% of the motor threshold intensity is preferred, more preferably from 40 to 85%, still more preferably from 50 to 80%.

Typically, the threshold current will be in the range of from 5 to 50 mA, more preferably from 7 to 40 mA, still more preferably from 10 to 30 mA. Threshold currents outside this range may be applicable, depending upon the subject, other stimulation parameters and the method of applying the pulses. The current applied during the conditioning pulse may be varied by adjusting the voltage, assuming other factors, such as the condition of the skin and tissue of the subject, remain constant.

Typically, the conditioning pulses may be applied at any suitable voltage, subject to the factors discussed above. As noted, the voltage may be varied to provide the required electrical current for the prevailing electrical resistance of the skin and tissue of the subject. A typical voltage for the conditioning pulse may be up to 150V, more preferably up to 140V, still more preferably up to 130V. A voltage of up to 120V is particularly suitable in many cases, taking a typical resistivity of the skin and tissue of the subject to be about 10 kOhm. In cases where the resistivity is reduced, for example when applying the electrical pulses to the skin of the subject by means of adhesive pads, the voltage required for the pulse will be significantly lower, for example about 30V when the skin resistivity is about 500 Ohm.

The conditioning pulse of the first step is applied for a continuous period of at least 0.5 milliseconds, preferably from 0.5 to 20 milliseconds, more preferably from 0.75 to 15 milliseconds, still more preferably from 1.0 to 10 milliseconds.

The conditioning pulse acts to condition and temporarily disable the sensory nerve fibres of the subject in the target area, to produce a rapid and short-lived analgesia of the target area, thereby to reduce the sensitivity of the subject to higher intensity pulses applied in the second step of the method. The intensity of the pulse is such that the subject is able to feel the pulse and is aware of an electrical pulse being applied. In this respect, the intensity of the pulse is selected such that it is above that needed to stimulate the sensory nerve fibres of the subject, but not to stimulate the motor nerve fibres. However, the intensity is below that at which contraction of the target muscles is triggered. The intensity and duration of the conditioning pulse are selected to ensure that the analgesic effect preferably has a duration of step two of the method. In this respect, it is believed that the mechanism giving rise to the analgesic effect is that of so-called 'gate control'.

The first step may comprise applying a single conditioning pulse to the subject. Alternatively, a plurality of conditioning pulses may be applied in the first step, with successive pulses being separated by a rest period. In this case, the rest period is preferably from 1 to 10 milliseconds, more preferably from 5 to 10 milliseconds.

The conditioning pulse may have any suitable waveform. Suitable waveforms include curved waveforms. In a preferred embodiment, the conditioning pulse has an initial portion during which the intensity of the pulse increases rapidly from zero to the maximum intensity, an intermediate portion in which the intensity of the pulse is kept substantially constant, and a final portion in which the intensity of the pulse is rapidly reduced to zero. It is particularly preferred that the conditioning pulse has a rectangular or square waveform.

The polarity of the conditioning pulse may be kept constant across successive conditioning pulses. Alternatively, the polarity of successive conditioning pulses may change. For example, the polarity of successive conditioning pulses may be reversed.

The conditioning pulse applied in the first step of the method is followed by electrostimulation of the muscles in the second step of the method. A rest period may be applied between the first and second steps. If applied, the rest period is preferably relatively short, in particular having a duration of from 50 to 750 microseconds, more preferably from 75 to 600 microseconds, still more preferably from 100 to 500 microseconds.

In the second step of the method, a plurality of stimulating electrical pulses are applied to the subject to stimulate contraction of the muscles in the target area. In order to achieve contraction of the target muscles, the intensity of the pulses in the second step is above the motor threshold intensity of the target muscles. Due to the analgesic effect of the conditioning pulse applied in the first step, the ability of the subject to tolerate the stimulating pulse applied is increased, in turn improving the efficacy of the treatment.

The stimulating pulses in the second step may be applied in any suitable pattern to provide the desired level of stimulation to the subject and induce the level of muscular contraction required. Suitable regimes for applying stimulating pulses in the second step are known in the art.

In a preferred embodiment, the stimulating electrical pulses applied in the second step of the method are so-called 'wide pulses', that is are of a longer duration compared with those of the prior art. In particular, the electrical pulses of the present invention have a duration of greater than 0.5 milliseconds. Preferably, the pulses have a duration of greater than 0.75 milliseconds, more preferably at least 0.85 milliseconds. By applying pulses having a minimum pulse width as aforementioned, it has been found that the contractions induced in the muscles of the subject more closely correspond to natural or voluntary muscle contractions performed by the subject themselves. This in turn results in a significantly improved action of the muscles in pumping blood through the muscle vasculature and the venous blood vessels. Further, it has been found that, by more closely reproducing natural muscle contractions, the electrostimulation is less fatiguing for the subject. It has also been found that a desired increase in blood flow can be achieved at lower current levels than the prior art.

Excessive pulse widths should preferably be avoided, as such electrical pulses can produce a strong bi-directional activation of motor axons. This will reduce the efficiency of the voluntary command through antidromic block of the motor nerves. This, in turn can result in a more rapid fatiguing of the muscles. In particular, the antidromic block will produce a reduced muscle contraction, resulting in an earlier onset of fatigue in the muscle, despite producing weaker contractions. Accordingly, it is preferred that the electrical pulses applied to the subject have a maximum width of 2 milliseconds, more preferably 1.75 milliseconds, still more preferably 1.5 milliseconds.

A pulse width in the range of from 0.5 to 2.0 milliseconds has been found to be advantageous, preferably from 0.6 to 1.8 milliseconds, more preferably from 0.7 to 1.75 milliseconds, still more preferably from 0.75 to 1.6 milliseconds. A pulse width in the range of from 0.75 to 1.5 milliseconds is particularly suitable, preferably from 0.8 to 1.4, still more preferably from 0.85 to 1.3 milliseconds. It has been found that a pulse width of from 0.9 to 1.2 milliseconds is particularly advantageous, more preferably from 0.95 to 1.1 seconds. A pulse width of about 1.0 milliseconds is a particularly preferred embodiment of the present invention.

The electrical pulses may be applied in any suitable pattern. It is preferred that the pulses are applied with suitable rest periods between pulses or groups of pulses. For example, the pulses may be applied singly, with consecutive pulses being separated by an inter-pulse rest period. The rest period between pulses is a period in which the intensity of the electrical stimulation being applied to the subject is below the level necessary to induce contraction of the target muscle or muscles. Preferably, zero electrical stimulation is applied to the subject during the rest period.

The length of the inter-pule rest period may be determined, at least in part, by the limitations of the apparatus being used to generate the pulses. The inter-pulse rest period may range from 50 microseconds to 300 microseconds, preferably from 60 to 250 microseconds, more preferably from 65 to 200 microseconds, still more preferably from 75 to 150 microseconds. An inter-pulse rest period of from 80 to 140 microseconds is particularly suitable, more preferably from 85 to 130 microseconds, still more preferably from 90 to 125 microseconds. An inter-pulse rest period of at least 100 microseconds is particularly preferred, for ease of construction and operation of the pulse generating apparatus.

More preferably, the stimulating pulses in the second step of the method of this invention are applied in groups, each group comprising two or more pulses separated by a first inter-pulse rest period. Consecutive groups of pulses are separated by a second inter-pulse rest period. The second inter-pulse rest period is preferably longer than the first inter-pulse rest period.

The length of the first inter-pulse rest period may be determined, at least in part, by the limitations of the apparatus being used to generate the pulses, as described hereinbefore.

The second inter-pulse rest period is the period of rest between successive groups of pulses. This rest period is preferably a sufficient length of time to allow the vasculature in the region being treated to refill with blood, in advance of the following muscle contraction. By allowing a sufficient rest period to substantially or wholly refill with oxygenated blood, the muscle fatigue is delayed and, as a result, the efficiency of the treatment in expelling and pumping blood is increased. The second inter-pulse rest period is preferably at least 10 milliseconds, more preferably at least 20 milliseconds, still more preferably at least 25 milliseconds. Details of a preferred rest period between pulses or groups of pulses inducing contraction in the muscles of the subject are described in more detail hereinbelow.

The ratio of each electrical pulse or group of pulses to the intervening rest period is preferably from 1:1 to 1:8, more preferably from 1:1 to 1:6, still more preferably from 1:1 to 1:4.

The train of stimulation pulses may be considered to have a duty cycle, that is the fraction of the total elapsed time of the train during which the pulses have an intensity sufficient to stimulate muscle contraction. The duty cycle may range from 5% to 75%, more preferably from 10% to 60%, still more preferably from 20% to 50%.

The groups of pulses may contain the same number of pulses or a different number of pulses. Preferably, the stimulating pulses in the second step of the method are applied in a plurality of groups, each group having the same number of pulses therein.

Each group of pulses preferably comprises at least two pulses, more preferably at least three pulses. Higher numbers of pulses may be applied in each group, for example four pulses, five pulses, up to ten pulses. However, a high number of pulses in a given group can reduce the efficiency of the electrostimulation in inducing pumping of blood from the venous blood vessels, as the subject is provided with insufficient rest periods to allow the veins to refill with blood. Accordingly, it is preferred that the number of pulses in each group is less than ten, more preferably less than eight, still more preferably less than six. A group of less than five pulses is preferred, with pulses being arranged in groups of three or triplets is particularly preferred.

The current level or intensity of the stimulating electrical pulses is above the motor threshold for the nerves within the target muscles and may be varied and selected to provide the desired level of muscle contraction, without being painful or uncomfortable to the subject. Factors affecting the current level to be applied include the condition of the subject and their muscles and the resistance of the skin or tissue of the subject to which the electrical pulses are being applied. The current level will also determine the stimulation intensity of the treatment. Typical peak current levels are in the range of from 20 to 100 mA, more preferably from 25 to 60 mA, still more preferably from 30 to 50 mA.

The intensity of the stimulating electrical pulses may be any intensity that is sufficient to produce the required contractions in the target muscles of the subject. Preferably, the intensity is at least 110% of the motor threshold intensity, more preferably at least 120% of the motor threshold intensity. Still more preferably, the intensity is at least 150% of the motor threshold intensity. The intensity may be up to 250% of the motor threshold intensity, preferably up to 200% of the motor threshold intensity.

Similarly, the voltage level to be applied will depend upon the prevailing conditions, such as the condition of the subject, the resistance of the skin or tissue of the subject and the stimulation intensity to be achieved. For a healthy subject, a typical skin resistance is from 1 to 10 kOhms, and may be lower if the skin is wet. In light of this, a typical peak voltage for the pulses may be up to 250 V, preferably from 20 to 160 V, more preferably from 25 to 150 V, still more preferably from 30 to 140 V. A peak voltage of up to 150 V may be applied, depending upon the intensity of the stimulation to be delivered to the muscles of the subject.

The pulses may be applied with voltage of a single polarity. Alternatively, stimulating pulses may be applied with an alternating polarity. The polarity of the voltage may alternate between consecutive single pulses or between consecutive groups of pulses.

The stimulation intensity of the electrostimulation may also be indicated in terms of the percentage of the maximum voluntary muscle contraction (MVC) achievable by the subject. A minimum stimulation intensity is 10% MVC, more preferably at least 15% MVC, still more preferably at least 20% MVC. A stronger stimulation intensity may be applied, so as to induce a stronger muscle contraction. Accordingly, a stimulation intensity of up to 40% MVC, more preferably up to 50% MVC may be applied. A stimulation intensity in excess of 50% MVC should preferably be avoided as this generally induces a rapid onset of muscle fatigue in the subject, reducing the efficacy of the electrostimulation session.

The electrostimulation may be applied by way of pulses of any suitable shape. For example, the variation of the voltage with time of each pulse may be in the form of a square wave. More preferably, the amplitude of the waveform of the pulses is modulated. Modulation of the pulses waveform is advantageous as it reduces the tendency for habituation of the muscles subject, whereby the response of the muscles to the electrical stimulation reduces over time. Any suitable signal may be applied to the pulses to modulate the amplitude of the waveform. Preferably, the modulation is achieved by applying a triangular signal or, more preferably, by applying a sine wave to the basic pulse waveform. The frequency of the modulation signal applied to the basic pulse waveform may vary, but is preferably from 0.5 to 2 Hz. Modulation frequencies of up to 4 Hz may be applied.

The depth of the modulation signal, that is the extent to which the amplitude of the basic waveform is varied, is preferably from 10 to 60%, more preferably from 15 to 50%.

The electrostimulation method of the present invention may be applied for any suitable length of time to achieve the desired level of pumping of blood from the veins of the subject, while avoiding excessive muscle fatigue. The electrostimulation is preferably applied for a period of at least 5 minutes, more preferably at least 10 minutes. The maximum length of an electrostimulation session will be determined by such factors as the condition of the subject and the onset of muscle fatigue. Typically, the electrostimulation session is up to 40 minutes in length, more preferably up to 30 minutes in length. A session time of from 15 to 25 minutes, more preferably about 20 minutes is advantageous. The sessions may be repeated at any suitable frequency, depending upon such factors as the condition of the subject.

To avoid habituation of the muscles of the subject, it is preferred that the pattern of pulses, in terms of pulse duration, the rest period between pulses, the number of pulses in each group of pulses, the modulation waveform applied to the pulses, and the rest period between groups of pulses is varied throughout the session. Preferably, a given pattern or train of pulses is repeated no more than four times, more preferably no more than three times, still more preferably no more than twice in any session. In one preferred embodiment, a given train of pulses is repeated no more than twice in any 20 minutes of electrostimulation.

As described hereinbefore, it is important to provide the muscles of the subject with an opportunity to rest between successive stimulating electrical pulses or groups of pulses. As noted, the muscle is being induced to contract by electrical pulse stimulation, in order to expel blood from the venous blood vessels. In particular, the muscle is contracting under the effects of the stimulation to pump blood against the hydrostatic forces back into the central circulation system of the subject and, ultimately, to the heart. After blood has been expelled from the blood vessels by the muscle contractions, there needs to follow a period of relaxation, during which the blood vessels, such as the veins, can refill with blood, before the next contraction. If insufficient time is allowed for the blood vessels to refill with blood, the muscles will fatigue more rapidly and subsequent muscle contractions will be less efficient in expelling and pumping blood.

Further, a sufficient rest period between muscle contractions is required for optimising muscle performance. The efficiency of muscle contractions depends both on the metabolism of the subject and the ability of the nerves and muscle fibres of the subject to be excited by stimulation. After single contractions, muscles tend to relax relatively quickly, that is within a period of 100 to 200 milliseconds. However, after repetitive contractions, either voluntary or invoked by external stimulation, a longer period is required to allow the muscle to fully relax. This period can be up to 1 second in length.

The energy for muscle contractions is derived by the muscle tissue from oxygen and macronutrients provided to the muscle by means of the arterial blood flow in the subject. A lack of sufficient oxygen and/or glycogen available to the muscles results in a rapid fatiguing of the muscles. Further, an accumulation of metabolites, such as lactate, can also enhance muscle fatigue in the subject. As a result, the efficient removal of metabolites by the venous blood flow is important in maintaining muscle performance. Therefore, repeated muscle contractions that have a rhythm falling within the rate of breathing of the subject, that is from 5 to 50 breaths per minute, and within the normal range of heart rates, that is from 50 to 150 beats per minute, will reduce premature fatigue of the muscles and will assist in maintaining an efficient and prolonged muscle pump function.

Depending upon the intensity of preceding muscle contractions, energy reserves for the muscle can be restored by nutrients supplied through the flow of arterial blood within a period of from 30 seconds to 5 minutes. It is not necessary to apply a rest period for this length of time and achieve full recovery of the muscles being stimulated. However, some rest will be required to maintain muscle performance in pumping blood through the venous system.

It has been found that the efficiency of the muscle contractions induced by electrostimulation can be maintained if the muscles are allowed to rest for a period of at least 1 second, during which the muscles of the subject being stimulated are allowed to relax.

During this rest period, one or more conditioning pulses, as hereinbefore described, may be applied to the subject, to induce or maintain the aforementioned analgesic effect.

The ratio of the period of electrical stimulation, that is each stimulating electrical pulse or group of pulses, to the intervening rest period is preferably from 1:1 to 1:8, more preferably from 1:1 to 1:6, still more preferably from 1:1 to 1:4. In one preferred embodiment, the ratio of the period of electrical stimulation to the rest period is about 1:1.

The duration of the rest period and the ratio of the rest period to the period of stimulation of the muscles will vary according to such factors as the condition of the muscles of the subject, the recent activity of the muscles, the metabolism of the subject, and the health of the subject.

The rest period is at least 1 second, to allow the venous blood vessels to fill with blood and to provide sufficient time for the muscles being stimulated to relax and recover to a sufficient level to maintain sufficient efficiency in pumping blood from the veins. The rest period may be up to 5 seconds, more preferably up to 4 seconds, still more preferably up to 3 seconds. In many cases, a rest period of from 1 to 2 seconds is appropriate, more preferably from 1 to 1.5 seconds. A rest period of about 1 second has been found to be suitable for the stimulation of many subjects.

The electrical pulses of both the first and second steps of the method of present invention are applied to the subject in a manner appropriate to stimulate the action of the muscle or muscle group being targeted. The electrical pulses may be applied using any suitable means. For example, the electrical pulses may be applied percutaneously to the subject, in particular by electrodes extending into the skin of the subject. More preferably, the electrical pulses are applied transcutaneously by means of electrodes or other electrical contact means applied to the skin of the subject.

In one embodiment of the invention, to induce venous blood flow, in particular the venous return, in the legs of the subject, the electrical pulses are applied to one or both feet of the subject, more preferably to the soles of one or both feet. A preferred embodiment of an apparatus for applying the electrostimulation to a subject is described in more detail hereinbelow.

The apparatus for providing the electrostimulation of the present invention to a subject generally comprises the following components, which will be known to the person skilled in the art.

The apparatus comprises means for providing an electrical stimulation cycle to the subject. The means for providing the electrical stimulation may be any suitable means for generating the electrical current and supplying the current to the subject. Suitable means are known in the art.

One system for providing electrical stimulation to the subject comprises a power supply unit for providing a supply to electricity. The power supply unit may be any suitable supply unit, preferably one connectable to a domestic electrical supply. The system may further comprise a processor for operating control electronics for providing a voltage. This in turn is provided to a transformer to step the voltage up to a level suitable for administering to the subject. The processor further operates a pulse control circuit, for generating electrical pulses of the required shape and duration.

The apparatus comprises means for delivering the electrical pulses to the subject. The electrical stimulation pulses may be applied to the subject in any suitable manner. For example, the pulses may be applied percutaneously, by way of one or more electrodes extending into the skin of the subject. More preferably, the apparatus comprises one or more contact members having a contact surface for location on the skin of the subject. In this way, the electrical pulses are delivered transcutaneously to the surface of the skin of the subject in the region of the muscles to be stimulated.

The means for delivering the electrical pulses to the subject is provided with a first portion connected to the electrically positive side of the system and a second portion connected to the electrically negative side of the system.

The method of the present invention may be employed to provide electrical stimulation pulses to the muscles in any part of the subject. In a particularly preferred embodiment, the method and apparatus are employed to provide electrical stimulation to the muscles of the legs of the subject, in particular the lower leg, more particularly the calves, ankle and foot of the subject. Accordingly, a particularly preferred embodiment is to provide the electrical pulses to the soles of either one or both feet of the subject.

In this embodiment of the present invention, a train of electrical pulses is applied to the foot of the subject. In particular, an electrical current is applied to the plantar surface of the foot, thereby first conditioning and inducing analgesia in the nerves and thereafter stimulating the plantar muscles of the foot and the muscles of the leg of the subject, in particular the lower leg. The electrical pulses are applied to the plantar surface of the foot through a contact member having a contact surface. The subject places their foot on the contact member of the apparatus such that the plantar surface of the foot is in contact with the contact surface. The contact surface is electrically conductive, allowing an electrical current to be provided to the plantar muscles of the foot from the apparatus. A contact surface may be applied to one foot of the subject or a contact surface may be applied to each of both feet.

The contact surface may have any suitable shape, so as to provide a sufficient contact with the plantar surface of the foot of the subject. Preferably, the contact surface is elongate, having a proximal end, disposed towards the user when in use, and a distal end opposite the proximal end. More preferably the contact surface is of a size and shape to accommodate the major portion of the plantar surface of the foot. It is particularly preferred for the contact surface to be of a sufficient size to accommodate the entire underside of the foot of the subject.

The contact surface may be formed from any suitable material that conducts the electrical current to the plantar surface of the foot of the subject. For example, the contact surface may be formed from a rubber composition comprising carbon, the carbon being present in sufficient amount to provide the requisite electrical conductivity. Alternatively, the contact surface may be formed from metal or from a plastic composition that is electrically conductive or provided with an electrically conductive coating. Other suitable materials for forming the contact member and the contact surface are known in the art.

The contact surface may be flat or substantially flat. Alternatively, the contact surface may be contoured to accommodate the contours of the plantar surface of the foot of the subject. In one embodiment, the contact surface is provided with one or more ridges thereon, the electrical current being provided to the ridges of the contact surface for conducting to the foot of the subject. Alternatively, the contact surface may be smooth or substantially smooth.

Embodiments of the present invention will now be described, by way of example only, having reference to the accompanying drawings, in which.

Figure 1:
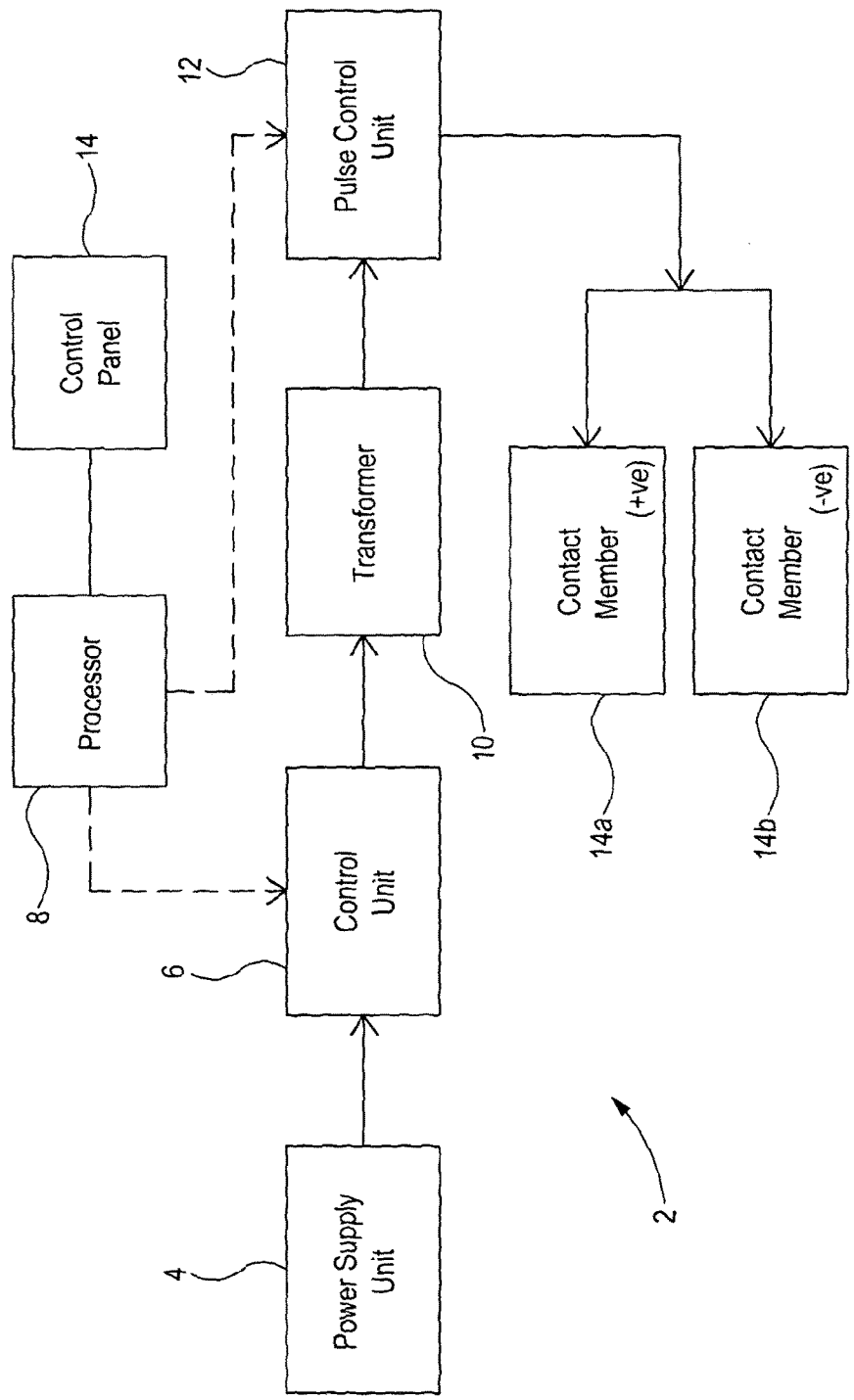
FIG. 1 is a schematic diagram of one embodiment of a system for generating electrical pulses for use in the apparatus of the present invention.

Referring to FIG. 1, there is shown a schematic diagram of one embodiment of a system for generating electrical pulses for the stimulation of the feet of a subject. The system, generally indicated as 2, is suitable for use in the method of the present invention. The system 2 is arranged for providing electrical stimulation to the plantar surfaces of the feet of a subject. However, the general aspects of the system may be used to provide electrical stimulation to muscles in other parts of the subject in like manner as described below.

The system 2 comprises a power supply unit 4, for example connectable to an electrical power supply, such as a domestic electrical supply. The power supply unit 4 outputs an electric current, the voltage of which is adjusted, as required by a control unit 6, under the action of a processor 8. The adjusted voltage is stepped up by a transformer 10, before being fed to a pulse control unit 12, also operated by the processor 8. The pulse control unit generates a pulsed electrical signal having the desired pulse shape and duration, under the action of the processor. The output of the pulse control unit 12 is connected to the first and second contact members 14a, 14b of the apparatus of FIG. 1. A control panel 14 provides a user interface for controlling the processor 8.

In use, by placing their feet on the contact surfaces of the contact members 14a, 14b, the user completes an electrical circuit, allowing the pulsed electrical signal to travel from one foot to the other and stimulate muscle contraction in the feet and legs of the user.

Figure 2:
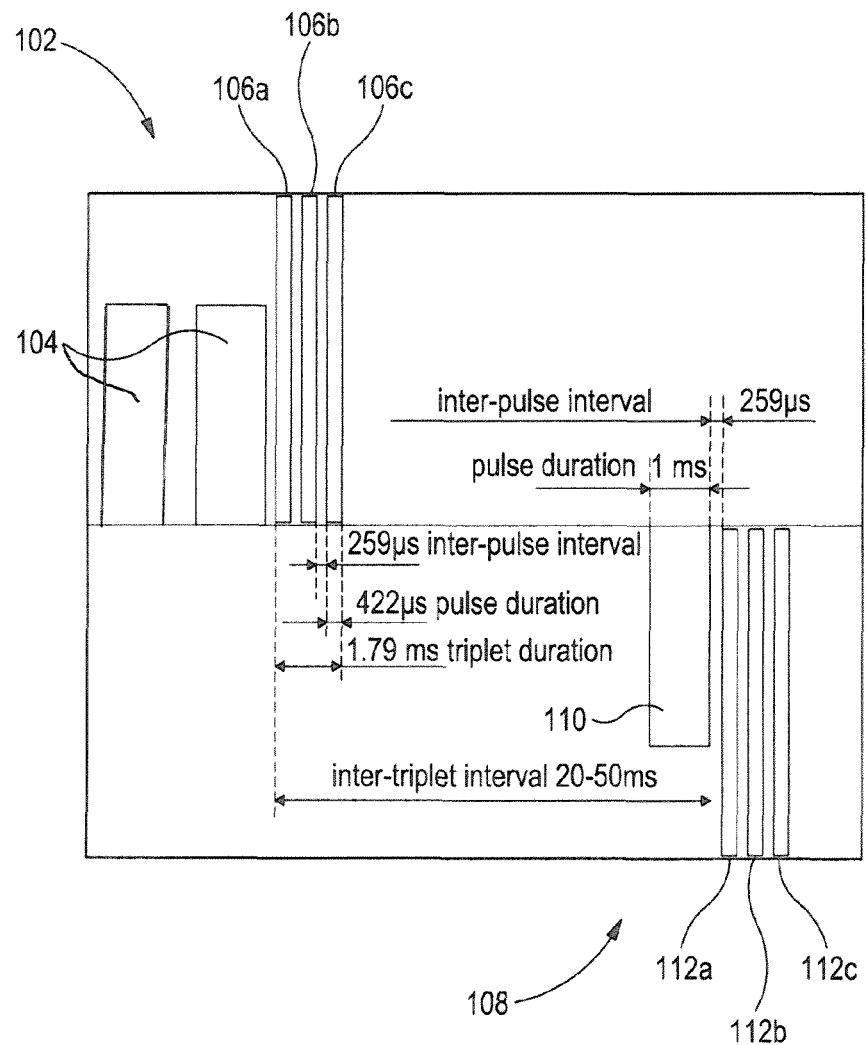
FIG. 2 is a graphical representation of a cycle of electrostimulation pulses according to an embodiment of the present invention.

Referring to FIG. 2, there is shown a graphical representation of a train of electrical pulses for applying to a subject to stimulate contraction of a target group of muscles, such as those of the lower leg. The pulses are represented as plots of voltage against time.

The train of pulses represented in FIG. 2 comprises a first group of pulses 102, comprising a conditioning pulse 104 and three stimulating pulses 106a, 106b and 106c, and a second group of pulses 108, comprising a conditioning pulse 110 and three stimulating pulses 112a, 112b and 112c. As can be seen, the pulses in the first group 102 are in the opposite polarity to those of the second group 104.

The pulses in the first and second groups 102, 108 are generally square in form, having a rapid increase in voltage from zero to a single nominal voltage, which is held for substantially the entire duration of the pulse, after which the voltage is rapidly decreased to zero.

Each conditioning pulse 104, 110 rises to a peak voltage of about 120V to provide a current intensity of from 10 to 30 mA and below the motor threshold intensity of the subject. The effect of each conditioning pulse 104, 110 is to generate a temporary analgesia in the target nerves, thereby reducing the sensitivity of the nerves to the stimulating pulses that follow. The analgesic effect generated by the conditioning pulse has a duration of at least the time taken to deliver the three subsequent stimulating pulses 106a-c, 112a-c.

The conditioning pulse 104, 110 has a duration of 1 millisecond.

A rest period immediately follows each conditioning pulse 104, 110 before the first of the stimulating pulses, during which rest period the voltage is substantially zero and no current is applied to the subject. The duration of the rest period between each conditioning pulse 104, 110 and the following stimulating pulse 106a, 112a may be in the range of from 100 to 300 microseconds. The rest period indicated in FIG. 2 is 259 microseconds.

Each conditioning pulse 104, 110 is followed by a series of three stimulating pulses 106a-c, 112a-c. Each stimulating pulse rises to a peak voltage of about 150V, with a skin resistivity of about 10 kOhm. At lower resistances, the peak voltage is reduced, for example to about 30 V in the case of a resistivity of about 500 Ohm. Each stimulating pulse has a duration of 422 microseconds. Peak voltages of up to 250 V may be applied during each stimulating pulse, depending upon the intensity of the stimulation to be applied to the subject. Successive stimulating pulses 106a-c, 112a-c are separated by a rest period of 259 microseconds, during which the voltage is substantially zero and no current is applied to the subject. The total duration of the group of three stimulating pulses 106, 112 is 1.79 milliseconds.

The conditioning pulses 104, 110 and the groups of stimulating pulses 106, 112 are arranged in time such that the interval between successive groups of stimulating pulses is from 20 to 50 milliseconds.

The pulse train shown in FIG. 2 is repeatedly applied to the subject, as described above, during a treatment session.

Figure 3:
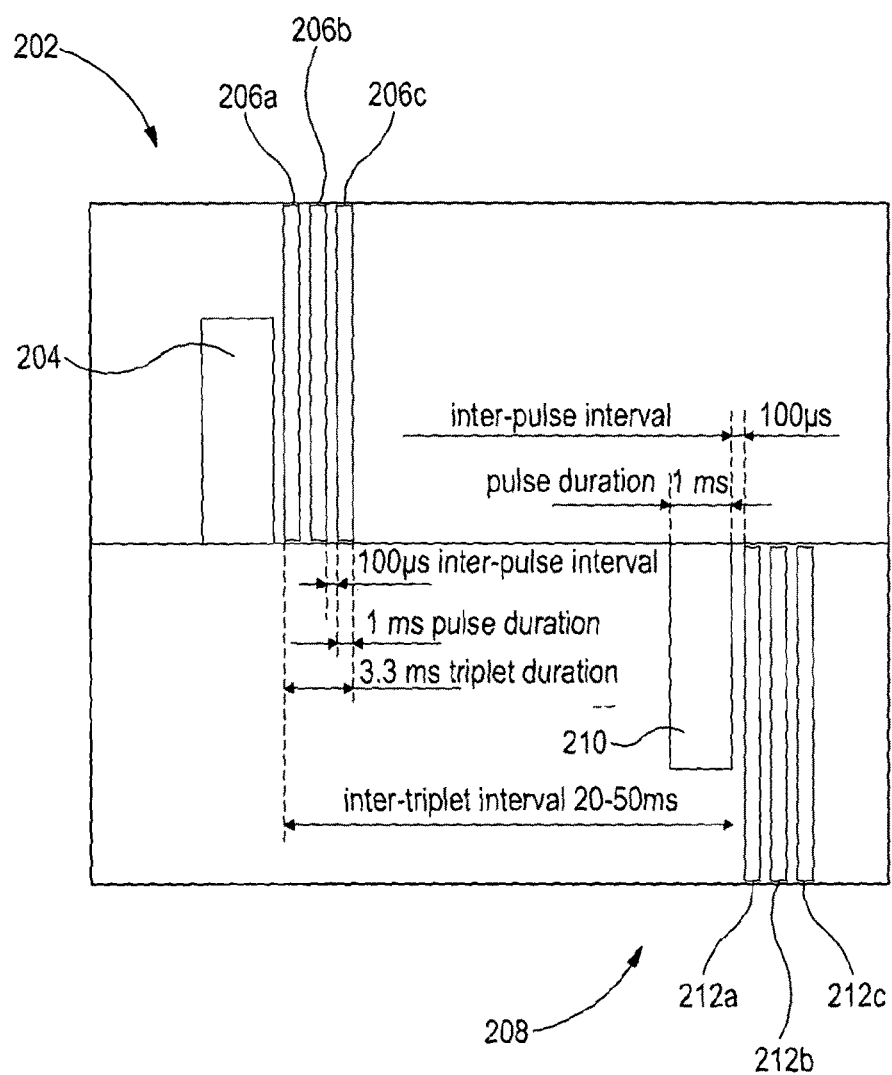
FIG. 3 is a graphical representation of a cycle of electrostimulation pulses according to a further embodiment of the present invention.

Referring to FIG. 3, there is shown a graphical representation of a train of electrical pulses for applying to a subject to stimulate contraction of a target group of muscles, such as those of the lower leg, according to a further embodiment of the present invention. The pulses are represented as plots of voltage against time.

The train of pulses represented in FIG. 3 comprises a first group of pulses 202, comprising a conditioning pulse 204 and three stimulating pulses 206a, 206b and 206c, and a second group of pulses 208, comprising a conditioning pulse 210 and three stimulating pulses 212a, 212b and 212c. As can be seen, the pulses in the first group 202 are in the opposite polarity to those of the second group 204.

The pulses in the first and second groups 202, 208 are generally square in form, having a rapid increase in voltage from zero to a single nominal voltage, which is held for substantially the entire duration of the pulse, after which the voltage is rapidly decreased to zero.

Each conditioning pulse 204, 210 rises to a peak voltage of about 120V to provide a current intensity of from 10 to 30 mA and below the motor threshold intensity of the subject. The effect of each conditioning pulse 204, 210 is to generate a temporary analgesia in the target nerves, thereby reducing the sensitivity of the nerves to the stimulating pulses that follow. The analgesic effect generated by the conditioning pulse has a duration of at least the time taken to deliver the three subsequent stimulating pulses 206a-c, 212a-c.

The conditioning pulse 204, 210 has a duration of 1 millisecond.

A rest period immediately follows each conditioning pulse 204, 210 before the first of the stimulating pulses, during which rest period the voltage is substantially zero and no current is applied to the subject. The duration of the rest period between each conditioning pulse 204, 210 and the following stimulating pulse 206a, 212a is 100 microseconds.

Each conditioning pulse 204, 210 is followed by a series of three stimulating pulses 206a-c, 212a-c. Each stimulating pulse rises to a peak voltage of about 150V, with a skin resistivity of about 10 kOhm. At lower resistances, the peak voltage is reduced, for example to about 30 V in the case of a resistivity of about 500 Ohm. Each stimulating pulse has a duration of 1.0 milliseconds. Peak voltages of up to 250 V may be applied during each stimulating pulse, depending upon the intensity of the stimulation to be applied to the subject. Successive stimulating pulses 206a-c, 212a-c are separated by a rest period of 100 microseconds, during which the voltage is substantially zero and no current is applied to the subject. The total duration of the group of three stimulating pulses 206, 212 is 3.3 milliseconds.

The conditioning pulses 204, 210 and the groups of stimulating pulses 206, 212 are arranged in time such that the interval between successive groups of stimulating pulses is from 20 to 50 milliseconds.

The pulse train shown in FIG. 3 is repeatedly applied to the subject, as described above, during a treatment session.

The invention claimed is:

1. A method of promoting flow of blood through a vascular system of a subject by electrostimulation of a group of one or more target muscles of the subject, the one or more target muscles having a motor threshold intensity, the method comprising:
   in a first step applying to the subject at least one conditioning electrical pulse having a duration of at least 0.5 milliseconds and an intensity below that effective in stimulating contraction of the target muscles of the subject; and
   in a second step applying one or more electrical pulses at an intensity sufficient to stimulate contraction of the target muscles of the subject;
   the subject having one foot having a plantar surface and a second foot having a plantar surface, wherein the electrical pulses are applied to the subject through a first contact surface contacting the plantar surface of one foot of the subject and a second contact surface contacting the plantar surface of the second foot of the subject, wherein the subject completes an electrical circuit allowing the electrical pulses to travel from one foot to the second foot.

2. The method according to claim 1, wherein the method further comprises determining the motor threshold intensity of the one or more target muscles of the subject.

3. The method according to claim 2, wherein determining the motor threshold intensity comprises applying to the one or more target muscles of the subject a plurality of pulses of increasing intensity while monitoring the subject for contraction of the one or more target muscles.

4. The method according to claim 2, wherein the conditioning electrical pulse is applied at an intensity of up to 80% of the motor threshold intensity.

5. The method according to claim 2, wherein the conditioning electrical pulse is applied at an intensity of greater than 50% of the motor threshold intensity.

6. The method according to claim 1, wherein the conditioning electrical pulse is applied for a period of from 1.0 to 10 milliseconds.

7. The method according to claim 1, wherein the first step comprises applying a plurality of conditioning electrical pulses, wherein successive conditioning pulses are separated by a rest period of from 1 to 10 milliseconds.

8. The method according to claim 1, wherein the conditioning electrical pulse is applied for a period of from 0.5 to 20 milliseconds.

9. The method according to claim 1, wherein the first and second steps are separated by a rest period of from 100 to 500 microseconds.

10. The method according to claim 1, wherein each pulse in the second step has a duration of greater than 0.85 milliseconds.

11. The method according to claim 1, wherein a plurality of pulses are applied in the second step, the pulses in the second step being applied in groups, each group comprising a plurality of pulses.

12. The method according to claim 11, wherein each group comprises less than 10 pulses.

13. The method according to claim 11, wherein successive pulses in each group of pulses are separated by a first rest period and successive groups of pulses are separated by a second rest period.

14. The method according to claim 13, wherein the first rest period is from 60 to 250 microseconds and the second rest period is at least 25 milliseconds.

15. The method according to claim 1, wherein the pulses in the second step are applied at an intensity of at least 150% of the motor threshold intensity.

16. The method according to claim 1, wherein the pulses applied in the second step are modulated by having a modulation waveform applied thereto.

17. A method of promoting flow of blood through a vascular system of a subject by electrostimulation of a group of one or more target muscles of a subject, the one or more target muscles having a motor threshold intensity, the method comprising:
   in a preliminary step determining the motor threshold intensity of the target muscles of the subject by applying an electrical pulse to the one or more target muscles and increasing the intensity of the pulse while monitoring the one or more target muscles for movement;
   in a first step applying to the subject an electrical pulse having an intensity below that effective in stimulating contraction of the target muscles of the subject to provide an analgesic effect; and
   in a second step applying one or more electrical pulses at an intensity sufficient to stimulate contraction of the target muscles of the subject;
   the subject having one foot having a plantar surface and a second foot having a plantar surface, wherein the electrical pulses are applied to the subject through a first contact surface contacting the plantar surface of one foot of the subject and a second contact surface contacting the plantar surface of the second foot of the subject, wherein the subject completes an electrical circuit allowing the electrical pulses to travel from one foot to the second foot.

* * * * *